United States Patent [19]

Swain

[11] Patent Number: 5,837,522

[45] Date of Patent: Nov. 17, 1998

[54] METHOD FOR INTRODUCING OXYGEN INTO A PROPAGATION ZONE OF FERMENTATION PROCESS

[76] Inventor: Robert L. B. Swain, 212 Fairfax Way, Williamsburg, Va. 23185

[21] Appl. No.: 795,421

[22] Filed: Feb. 4, 1997

[51] Int. Cl.$^6$ .............................. C12N 1/00; C12N 1/02; C12M 1/36

[52] U.S. Cl. ........................................ 435/243; 435/289.1

[58] Field of Search .................................. 435/243, 289.1

[56] References Cited

U.S. PATENT DOCUMENTS

| | | |
|---|---|---|
| 3,847,750 | 11/1974 | Ridgway, Jr. et al. . |
| 4,019,962 | 4/1977 | Allen et al. . |
| 4,169,010 | 9/1979 | Marwil . |
| 4,456,622 | 6/1984 | Maselli et al. . |
| 4,670,397 | 6/1987 | Wegner et al. . |
| 4,952,503 | 8/1990 | Granstedt . |

*Primary Examiner*—Leon B. Lankford, Jr.
*Attorney, Agent, or Firm*—Joy L. Bryant

[57] ABSTRACT

A method for introducing oxygen into a propagation zone of a fermentation process is provided. A propagation zone comprising a liquid ferment and microorganisms is provided. A portion of the liquid ferment is removed from the propagation zone and a molecular oxygen source is introduced into the removed liquid ferment to form a mixture comprising an oxygenated liquid ferment and non-dissolved gases. The oxygenated liquid ferment and the non-dissolved gases are separated and the non-dissolved gases are vented. The oxygenated liquid ferment is introduced to the propagation zone to be used by the microorganisms for reproduction and growth. In an additional step, carbon dioxide gas is recovered from the propagation zone.

12 Claims, 1 Drawing Sheet

METHOD FOR INTRODUCING OXYGEN INTO A PROPAGATION ZONE OF FERMENTATION PROCESS

FIELD OF THE INVENTION

The present invention relates to fermentation processes. In particular, the invention relates to a method for introducing oxygen into a propagation zone of a fermentation process.

BACKGROUND OF THE INVENTION

Fermentation processes have been found to be useful for producing a variety of products. These products include ethanol, acetic acid and single-cell protein materials which may be used as food supplements. In addition, in all aerobic fermentation processes, carbon dioxide gas is produced as a byproduct from the oxidative breakdown of glucose. In anaerobic fermentation processes, such as those involving the production of ethanol from glucose, a small amount of oxygen is required for growth of the fermenting organism and carbon dioxide gas is produced as a byproduct. In turn, it is often desirable to recover the carbon dioxide gas for future use in such products as carbonation of soft drinks and for quick freezing of meat products.

Most of the microorganisms, such as yeast or bacteria, which are used in fermentation processes use small quantities of oxygen for growth and reproduction, and some use large quantities of oxygen for metabolism. Thus, there is a need to enhance the exchange of oxygen between the microorganisms and the liquid ferment. In order to satisfy this need, many processes and different apparatuses have been proposed. To maintain high fermentation efficiencies in commercial fermentation, oxygen is supplied as a molecular oxygen-containing gas free of any stray microorganisms, into the culture media under conditions which allow for maximum contact of the oxygen with the culture media. This is done to dissolve as much oxygen into the aqueous media as possible, as well as to assist in providing heat transfer. Unfortunately, direct introduction of oxygen into the culture media results in increased contamination of the carbon dioxide byproduct.

High oxygen transfer rates have been achieved heretofore by conducting a fermentation process as a foam type process. Such a process provides a high surface area for contact between the liquid phase and the gas phase. In addition, the foam process has been found to be useful in order to obtain a high rate of oxygen transfer from the gas phase into the aqueous phase, and at the same time to assist in obtaining a good rate of removal of carbon dioxide and heat from the aqueous medium to the gas phase which then is exhausted for such use as may be suitable. However, the carbon dioxide byproduct is typically contaminated with remnants of the gases which have been introduced into the aqueous media.

Marwil (U.S. Pat. No. 4,169,010) discloses a process for improved oxygen utilization in aerobic fermentation conditions by using the exhaust gas from the fermentation section to oxygenate the return lean stream. This is done in addition to supplying a molecular oxygen source into the lower area of the fermentor section. In this process, rich culture media, rich in single cell protein (SCP), is removed continuously from the fermentation section. The cellular SCP materials are separated, and the lean ferment is fed back to the absorber section through the gas-contacting zone of the absorber section. In the absorber section, this return liquid stream of lean ferment is contacted with exhaust gas leaving the fermentation section, thus enriching the return (recycle) lean stream in oxygen, since the exhaust gases are still relatively high in unconsumed oxygen. Makeup water and nutrients, including minerals, also are fed into the system through the gas-contacting zone of the absorber section so that these, too, become enriched in oxygen prior to actually entering the fermentation section. Although the exhaust gases are relatively high in unconsumed oxygen, when the oxygen is passed through the absorber section, there is a tendency for carbon dioxide, which is also present, to displace the oxygen. This process not only contaminates the carbon dioxide but also causes the return stream to be depleted in oxygen.

Wegner et al. (U.S. Pat. No. 4,670,397) disclose a fermentation apparatus suitable for use in any aqueous, aerobic fermentation process, which apparatus comprises a fermentor vessel shell having heat exchange means disposed therein such that the heat exchange means is specifically oriented within the fermentor vessel both with respect to the angle of repose of the heat exchange means relative to the axis of the vessel and with respect to the volume of the vessel occupied by the heat exchange means. The fermentor vessel is further equipped with an agitation means which is positioned within the unobstructed zone of the vessel, i.e., that portion of the vessel not occupied by the heat exchange means. Gas is introduced into the vessel along with a carbon and energy source and nutrient media. In addition, there is an outlet means for removal of product and removal of off-gases. This arrangement provides both high heat exchange and high oxygen transfer capabilities. However, since the oxygen is introduced directly into the vessel, the carbon dioxide byproduct is contaminated with oxygen which escapes from the nutrient media.

In the aforementioned fermentation processes, oxygen is introduced directly into the fermentation tank. Since oxygen is not as soluble in liquid as carbon dioxide, much of the oxygen, plus most of the nitrogen when air is used as the source of oxygen, bubbles to the top of the tank where it mixes with and contaminates the carbon dioxide gas which is being produced. When trying to recover the carbon dioxide gas, these contaminants are undesirable and cause increased capital or operating costs of the carbon dioxide processing equipment. In order to facilitate transportation and storage of the carbon dioxide gas, it must be compressed and liquefied. If gases such as oxygen and nitrogen are present, the carbon dioxide liquefication temperature and pressure is adversely effected. In turn, larger compressors and higher operating pressures are required, thus increasing energy consumption. Moreover, the presence of these non-condensable gases reduces the overall yield of carbon dioxide gas because much of the carbon dioxide gas is lost when the non-condensable gases are vented from the system.

SUMMARY OF THE INVENTION

An object of the present invention is to provide a method for introducing oxygen into a propagation zone of a fermentation process which will minimize contamination of the carbon dioxide byproduct.

Another object of the present invention is to provide a method for introducing oxygen into a propagation zone of a fermentation process which may be used with currently existing fermentation apparatuses.

Another object of the present invention is to provide a method for introducing oxygen into a propagation zone of a fermentation process wherein molecular oxygen is entrained in the liquid ferment before introduction into the propagation zone.

By the present invention, a method for introducing oxygen into a propagation zone of a fermentation process is provided. A propagation zone comprising a liquid ferment and microorganisms is provided. A portion of the liquid ferment is removed from the propagation zone. A molecular oxygen source is introduced into the liquid ferment which has been removed to form a mixture of an oxygenated liquid ferment and non-dissolved gases. The oxygenated liquid ferment is separated from the non-dissolved gases and the non-dissolved gases are vented. The oxygenated liquid ferment is then introduced into the propagation zone. As an additional step to the method, carbon dioxide gas is recovered from the propagation zone.

In a preferred embodiment of the present invention, oxygen is introduced into a propagation zone of a fermentation process by providing a propagation zone comprising a liquid ferment and microorganisms. A portion of the liquid ferment is pumped from the propagation zone and air is injected through a sparger at an absolute pressure greater than about 1 atmosphere into the liquid ferment which has been pumped from the propagation zone. This forms a mixture of an oxygenated liquid ferment and non-dissolved gases. The mixture is cooled by passing it through a heat exchanger. Next, the oxygenated liquid ferment is separated from the non-dissolved gases using gravity and the non-dissolved gases are vented to a scrubber. The oxygenated liquid ferment is introduced into the propagation zone. An additional step to the process involves recovering carbon dioxide gas from the propagation zone.

DETAILED DESCRIPTION OF THE INVENTION

The present invention is a method for introducing oxygen into a propagation zone of a fermentation process. A typical fermentation process has two zones: a propagation zone and a fermentation zone. For the purpose of this disclosure and the appended claims, a propagation zone is defined as any location in the fermentation process where oxygen is introduced into the process for the purpose of promoting reproduction and growth of the fermenting microorganisms. Such a zone is not limited to one vessel. It is also known that primary fermentation occurs at the same time as propagation of the microorganisms in the propagation zone. A fermentation zone is defined as that portion of the fermentation process wherein the substrate, for example starch or sugar, is converted to the primary fermentation product, such as ethanol or acetic acid. Although some reproduction and growth of microorganisms may also occur in the fermentation zone, such reproduction and growth of the microorganisms is not normally encouraged in this zone by the introduction of oxygen unless the primary fermentation product is the microorganism itself, as in the case with single cell protein production.

The method of the present invention may be applied to both a batch or continuous fermentation process. Preferably, this method is designed for use in a continuous fermentation process where there are multiple vessels, and typically only one or two of these vessels are used for growth and reproduction of the fermentation microorganisms. In a continuous process, the return stream may be directed back into the originating vessel, another vessel in the propagation zone, or on to the fermentation zone.

Figure 1:
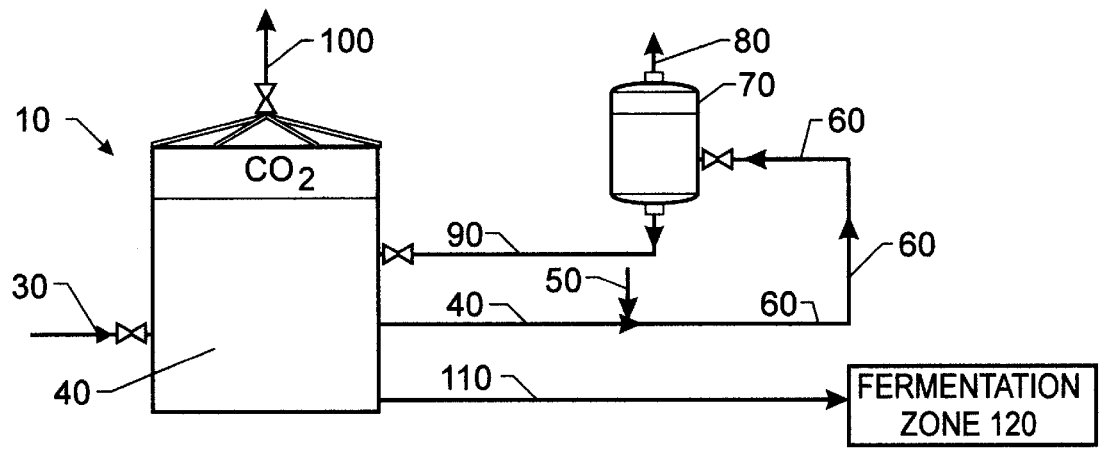
FIG. 1 is a schematic flow plan of an embodiment of the invention.
Figure 2:
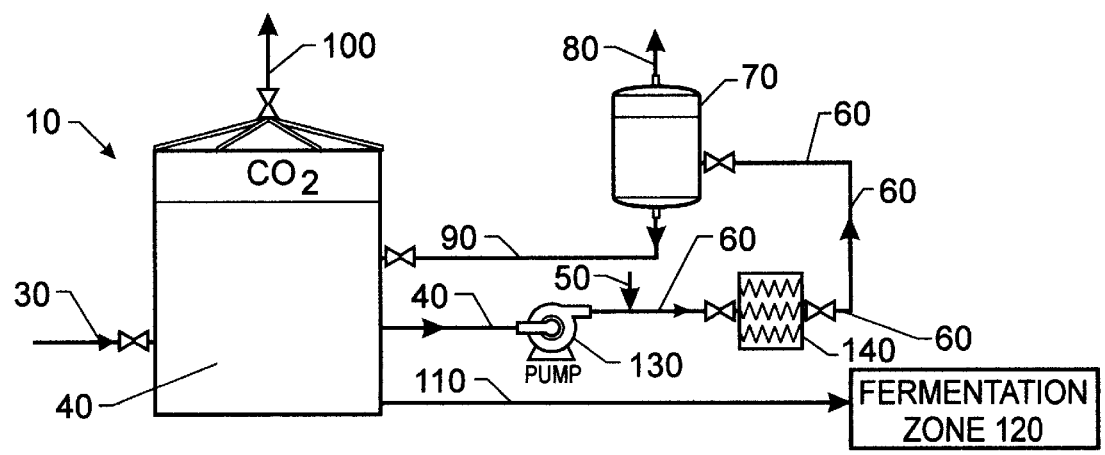
FIG. 2 is a schematic flow plan of a preferred embodiment of the invention.

Referring now to FIGS. 1 and 2, where like parts are numbered similarly, a propagation zone 10 is shown where the primary fermentation substrate 30 is charged into a vessel to make up a propagation zone comprising a liquid ferment 40 and microorganisms. Examples of the liquid ferment include but are not limited to aqueous substrates containing a feedstock such as glucose and a primary product such as ethanol or acetic acid. Any microorganism which metabolizes the feedstock into the primary product and requires oxygen during its reproduction and growth phase may be used for the present invention. In particular, yeast such as: the food yeast known as Candida utilis (Torula yeast); the yeast used in the production of ethanol known as saccharomyces cerevisiae, saccharomyces fragilis; and the bacteria used for the production of vinegar known as acetobacter. Although only one propagation vessel is shown in the propagation zone, there may be more than one vessel in series or parallel depending on the plant design.

A portion of the liquid ferment 40 is removed from the propagation zone. Removal of this liquid may be as simple as opening a valve manifold and allowing the liquid to flow into an external piping system, or it may be removed using a pump 130, such as a centrifugal pump. For the purpose of the present invention, a portion is defined as the volumetric rate of liquid removal from the propagation zone. This rate is established by the oxygen requirements of the fermentation microorganisms and, in the preferred embodiment where cooling of the liquid ferment occurs simultaneously, by the amount of heat removal required. The volume removed per minute preferably ranges from about 0.1% to about 10% of the total vessel volume.

Once a portion of the liquid ferment 40 is removed from the propagation zone, a molecular oxygen source 50 is introduced into the removed liquid ferment 40. The molecular oxygen source 50 may be introduced using any method known to those skilled in the art whereby oxygen is entrained in the liquid ferment to form a mixture 60 comprising an oxygenated liquid ferment and non-dissolved gases. The object is to dissolve the molecular oxygen in the liquid ferment without producing a lot of large bubbles. Smaller bubbles provide for a higher surface area, creating greater contact between the liquid and the gas, and providing enhanced oxygen absorption at the interface. For the present invention, air is the preferred molecular oxygen source. However, any molecular oxygen source known to those skilled in the art is suitable. Preferably, the air is injected into the liquid ferment through a sparger at an absolute pressure greater than about 1 atmosphere. Introducing the molecular oxygen source under pressure allows for quicker absorption of the molecular oxygen thus increasing the overall concentration of oxygen present in the liquid ferment. This is desirable since carbon dioxide, which is also present, is more easily absorbed than oxygen and has a tendency to displace oxygen.

Preferably, the mixture comprising the oxygenated liquid ferment and non-dissolved gases 60 is cooled by passing it through a heat exchanger 140. Any heat exchanger known to those skilled in the art may be used, but in particular a plate and frame heat exchanger is suitable for the present invention. The plate and frame heat exchanger is comprised of many flat plates with corrugated surfaces that fit together. One liquid passes between one set of plates and another liquid passes the opposite direction through another set of plates, etc. This action causes a shearing action on the liquid and serves well in breaking any large bubbles which may have been introduced by the sparger, thus allowing the liquid to become saturated with molecular oxygen. Moreover, this saturation effect is also enhanced by the cooled liquid which has a greater capacity for dissolved oxygen at lower temperatures.

Alternatively, the oxygenated liquid ferment may also be cooled by a conventional shell-and-tube heat exchanger, by placing a cooling jacket around the process piping, or by any other heat transfer mechanism known to those skilled in the art. If no heat exchanger is to be used, then additional residence time in the process piping is required to permit adequate dissolution of the molecular oxygen. This is accomplished by constructing the process piping at a length that is sufficient to provide the desired contact time between the liquid ferment and the molecular oxygen, and by controlling the volume of the oxygen containing gas that is introduced into the liquid ferment. The optimum length of the piping depends on the pressure and temperature of the liquid ferment, the concentration of oxygen in the oxygen source, the size of the gas bubbles, and the ratio of gas bubble volume to liquid volume. In practice, a piping length sufficient to provide from about 1 to about 30 seconds of contact time is typically needed, and other relevant parameters are adjusted to obtain the desired dissolved oxygen content in the liquid ferment.

The mixture 60 is separated using any method known to those skilled in the art, such as centrifugal separation or gravity separation. Preferably, the separation takes place using gravity or in what is known as a knock-out drum 70. The oxygenated liquid ferment and the non-dissolved gases undergo gravity separation to separate the two phases. The non-dissolved gas phase 80 contains a small amount of carbon dioxide along with any undissolved components from the molecular oxygen source such as oxygen and nitrogen. These gases are preferably vented to a scrubber to remove any volatile organic compounds from the gas stream prior to release to the atmosphere.

The oxygenated liquid ferment 90 is returned to the propagation zone 10 where the oxygen is metabolized by the microorganisms. The carbon dioxide byproduct 100 is recovered and condensed to be used by other industries. Since oxygen is not directly introduced into the propagation zone, the carbon dioxide recovered from the propagation zone has much less contamination than carbon dioxide which is produced following standard fermentation processes. A second stream of liquid ferment 110 is removed from the propagation zone and piped into the fermentation zone 120 where the microorganisms produce the primary fermentation product.

What is claimed as new and desired to be secured by Letters Patent of the United States is:

1. A method for introducing oxygen into a propagation zone of a fermentation process, the method comprising the steps of:
   a) providing a propagation zone comprising a liquid ferment and microorganisms;
   b) removing a portion of the liquid ferment from the propagation zone;
   c) introducing a molecular oxygen source into the removed liquid ferment to form a mixture comprising an oxygenated liquid ferment and non-dissolved gases;
   d) separating the oxygenated liquid ferment from the non-dissolved gases;
   e) venting the non-dissolved gases; and
   f) introducing the oxygenated liquid ferment into the propagation zone.

2. A method for introducing oxygen into a propagation zone of a fermentation process according to claim 1, the method further comprising the step of recovering carbon dioxide gas from the propagation zone.

3. A method for introducing oxygen into a propagation zone of a fermentation process according to claim 1, wherein the liquid ferment is removed from the propagation zone by pumping.

4. A method for introducing oxygen into a propagation zone of a fermentation process according to claim 1, wherein the molecular oxygen source is air.

5. A method for introducing oxygen into a propagation zone of a fermentation process according to claim 1, wherein the molecular oxygen source is introduced into the removed liquid ferment by injecting the molecular oxygen source through a sparger.

6. A method for introducing oxygen into a propagation zone of a fermentation process according to claim 1, wherein the molecular oxygen source is introduced into the removed liquid ferment at an absolute pressure greater than about 1 atmosphere.

7. A method for introducing oxygen into a propagation zone of a fermentation process according to claim 1, further comprising the step of cooling the mixture after step c.

8. A method for introducing oxygen into a propagation zone of a fermentation process according to claim 7, wherein the mixture is cooled by passing mixture through a heat-exchanger.

9. A method for introducing oxygen into a propagation zone of a fermentation process according to claim 1, wherein the oxygenated liquid ferment is separated from the non-dissolved gases using gravity.

10. A method for introducing oxygen into a propagation zone of a fermentation process according to claim 1, wherein the non-dissolved gases are vented to a scrubber.

11. A method for introducing oxygen into a propagation zone of a fermentation process, the method comprising the steps of:
   a) providing a propagation zone comprising a liquid ferment and microorganisms;
   b) pumping a portion of the liquid ferment from the propagation zone;
   c) injecting air through a sparger at an absolute pressure greater than about 1 atmosphere into the pumped portion of the liquid ferment to form a mixture of an oxygenated liquid ferment and non-dissolved gases;
   d) cooling the mixture by passing the mixture through a heat exchanger;
   e) separating the oxygenated liquid ferment from the non-dissolved gases using gravity;
   f) venting the non-dissolved gases to a scrubber; and
   g) introducing the oxygenated liquid ferment into the propagation zone.

12. A method for introducing oxygen into a propagation zone of a fermentation process according to claim 11, the method further comprising the step of recovering carbon dioxide gas from the propagation zone.

* * * * *